United States Patent
Watanabe et al.

(10) Patent No.: US 11,980,493 B2
(45) Date of Patent: May 14, 2024

(54) IMAGE PROCESSING APPARATUS, IMAGING SYSTEM, IMAGE PROCESSING METHOD, AND STORAGE MEDIUM

(71) Applicants: Taishi Watanabe, Tokyo (JP); Akira Kinoshita, Tokyo (JP); Masahiro Takada, Tokyo (JP); Shigenori Kawabata, Tokyo (JP)

(72) Inventors: Taishi Watanabe, Tokyo (JP); Akira Kinoshita, Tokyo (JP); Masahiro Takada, Tokyo (JP); Shigenori Kawabata, Tokyo (JP)

(73) Assignees: Ricoh Company, Ltd., Tokyo (JP); National University Corporation Tokyo Medical and Dental University, Tokyo (JP)

( * ) Notice: Subject to any disclaimer, the term of this patent is extended or adjusted under 35 U.S.C. 154(b) by 165 days.

(21) Appl. No.: 17/305,890

(22) Filed: Jul. 16, 2021

(65) Prior Publication Data
US 2022/0031276 A1     Feb. 3, 2022

(30) Foreign Application Priority Data

Jul. 31, 2020  (JP) ................. 2020-131129
Mar. 18, 2021  (JP) ................. 2021-044354

(51) Int. Cl.
*A61B 6/00*    (2024.01)
*G06V 10/40*   (2022.01)

(52) U.S. Cl.
CPC .......... *A61B 6/5258* (2013.01); *A61B 6/5247* (2013.01); *G06V 10/40* (2022.01)

(58) Field of Classification Search
CPC ... A61B 6/5241; A61B 6/5247; A61B 6/5258; A61B 6/547; A61B 6/582; A61B 6/5223;
(Continued)

(56) References Cited

U.S. PATENT DOCUMENTS 8,620,055 B2 *  12/2013  Barratt ............... G06T 7/35
                                                     378/4
10,433,758 B2   10/2019  Kawabata
(Continued)

FOREIGN PATENT DOCUMENTS

JP    2014-057664    4/2014
JP    2018-011952    1/2018
(Continued)

OTHER PUBLICATIONS

Extended European Search Report for 21186878.1 mailed on Nov. 24, 2021.
(Continued)

*Primary Examiner* — Dani Fox
*Assistant Examiner* — Soorena Kefayati
(74) *Attorney, Agent, or Firm* — IPUSA, PLLC

(57) ABSTRACT

An image processing apparatus includes a processor programmed to obtain a first radiation image of a subject captured from a first direction, obtain a second radiation image of the subject captured from a second direction that intersects the first direction, and either correct one of the first radiation image and the second radiation image based on positional information of a device for capturing the one of the first radiation image and the second radiation image, or correct another one of the first radiation image and the second radiation image based on information on a position of a specific region of the subject obtained from the one of the first radiation image and the second radiation image.

13 Claims, 10 Drawing Sheets

(58) Field of Classification Search
CPC ... A61B 6/5235; A61B 6/5217; A61B 6/5264; A61B 6/5211; A61B 6/242; A61B 6/4007; A61B 6/02; A61B 6/022; A61B 6/025; A61B 6/027; A61B 6/40; A61B 6/00; A61B 6/501; A61B 6/506; A61B 6/52858; A61B 5/242; G06V 10/40

See application file for complete search history.

(56) References Cited

U.S. PATENT DOCUMENTS

| | | | | |
|---|---|---|---|---|
| 2005/0195945 | A1* | 9/2005 | Gotoh | A61B 6/547 378/197 |
| 2005/0212515 | A1* | 9/2005 | Watanabe | G01V 15/00 324/248 |
| 2011/0069812 | A1* | 3/2011 | Takahashi | A61B 6/4464 378/21 |
| 2013/0051523 | A1* | 2/2013 | Davydov | G16H 50/20 378/62 |
| 2015/0193948 | A1* | 7/2015 | Kawamura | G06T 7/0002 382/132 |
| 2015/0366529 | A1* | 12/2015 | Shimizu | A61B 6/12 378/62 |
| 2016/0296195 | A1* | 10/2016 | Abe | A61B 6/542 |
| 2018/0008223 | A1* | 1/2018 | Yamagata | A61B 6/5211 |
| 2018/0028138 | A1* | 2/2018 | Oh | A61B 6/5235 |
| 2018/0140215 | A1* | 5/2018 | Kawabata | A61B 5/242 |
| 2019/0005660 | A1* | 1/2019 | Kinoshita | G06T 7/337 |
| 2019/0142356 | A1* | 5/2019 | Nakaya | A61B 6/00 378/98.8 |
| 2019/0167135 | A1 | 6/2019 | Okada et al. | |
| 2019/0223817 | A1* | 7/2019 | Kawabata | A61B 6/5247 |
| 2020/0069265 | A1* | 3/2020 | Joung | A61B 6/4085 |
| 2020/0069276 | A1* | 3/2020 | Yoshida | A61B 6/504 |
| 2020/0289079 | A1* | 9/2020 | Tanno | A61B 6/547 |

FOREIGN PATENT DOCUMENTS

| | | |
|---|---|---|
| JP | 6513798 | 5/2019 |
| JP | 2019-098156 | 6/2019 |
| JP | 2021-006243 | 1/2021 |
| WO | 2020/262401 | 12/2020 |

OTHER PUBLICATIONS

Close R et al.: "Automatic correction of biplane projection imaging geometry", Medical Physics, Aip, Melville, NY, US vol. 23, No. 1, Jan. 1, 1996 (Jan. 1, 1996), pp. 133-139, XP000554242.

Satoshi Sumiya et al.: "Magnetospinography visualizes electrophysiological activity in the cervical spinal cord", Scientific Reports, vol. 7, No. 1, May 19, 2017 (May 19, 2017), XP055449754.

Japanese Office Action for 2021-044354 mailed on Dec. 26, 2023.

* cited by examiner

FIG.9
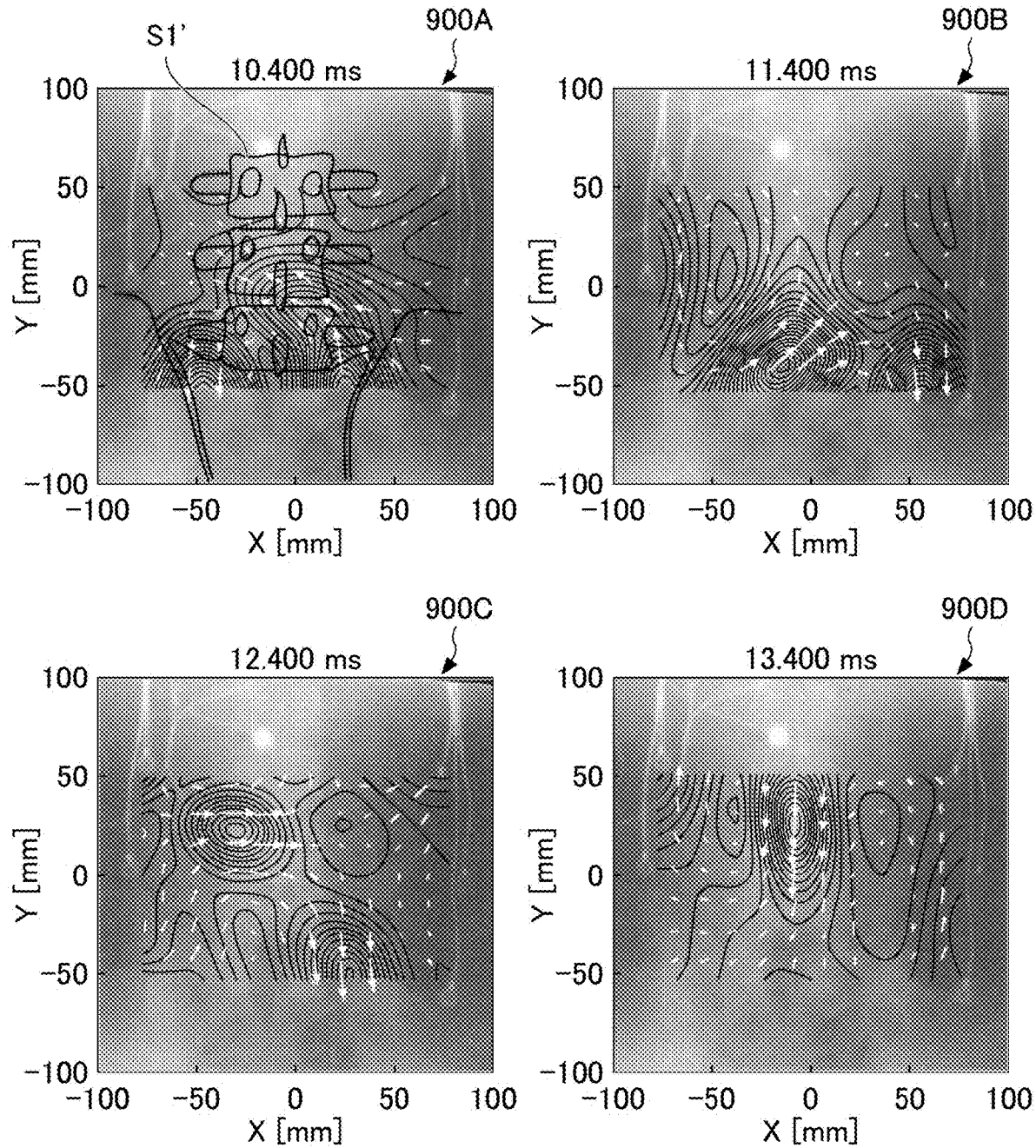
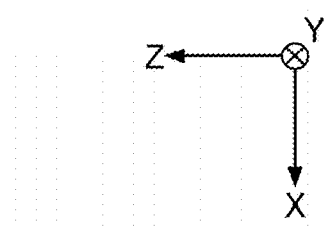

FIG.10
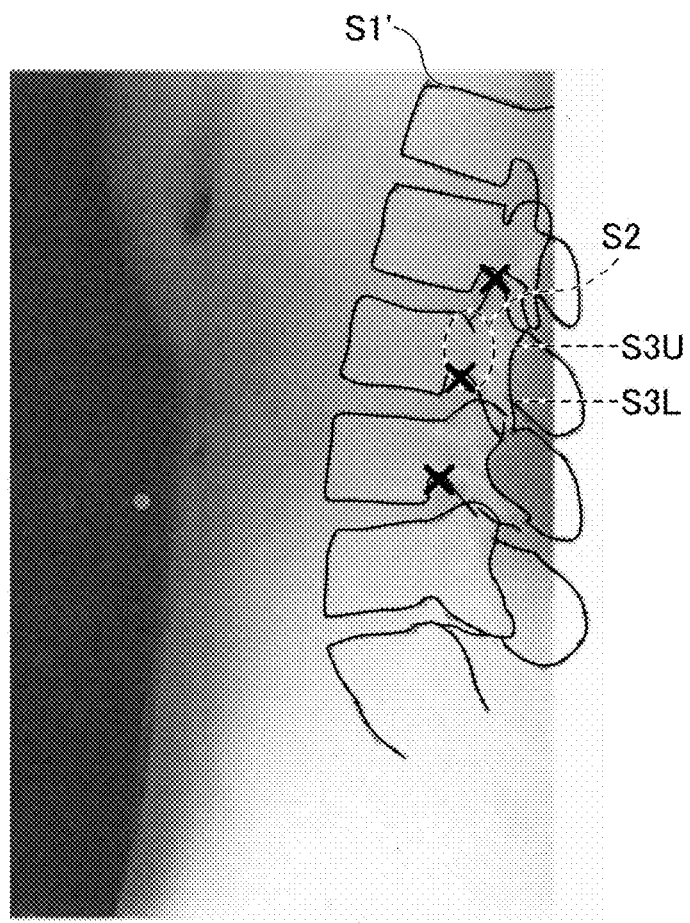
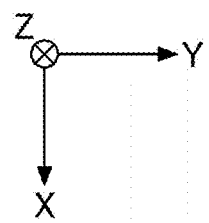

FIG.11
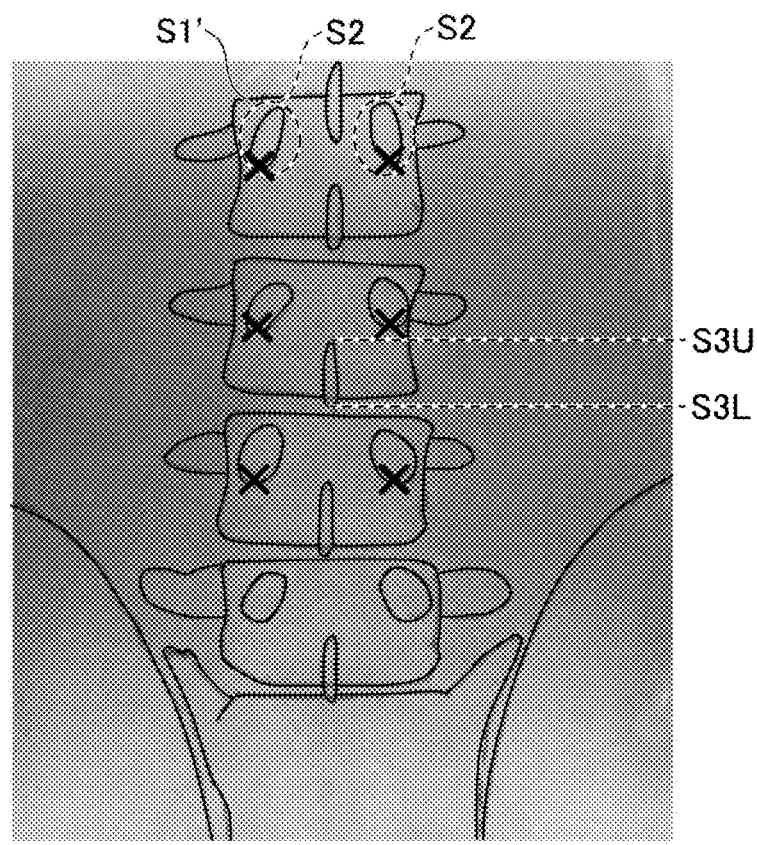
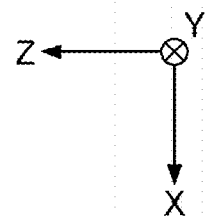

IMAGE PROCESSING APPARATUS, IMAGING SYSTEM, IMAGE PROCESSING METHOD, AND STORAGE MEDIUM

CROSS-REFERENCE TO RELATED APPLICATIONS

The present application claims priority under 35 U.S.C. § 119 to Japanese Patent Application No. 2020-131129, filed on Jul. 31, 2020 and Japanese Patent Application No. 2021-044354, filed on Mar. 18, 2021. The contents of which are incorporated herein by reference in their entirety.

BACKGROUND OF THE INVENTION

1. Field of the Invention

The present invention relates to an image processing apparatus, an imaging system, an image processing method, and a storage medium.

2. Description of the Related Art

Japanese Patent No. 6513798 describes a biometric information measuring apparatus that includes a biomagnetism detector and a radiation photoconductor positioned in an opposite direction from the direction in which a radiation irradiation unit is positioned relative to the subject, and is capable of both capturing a radiation image of the subject and detecting biomagnetism of the subject.

However, in the technology disclosed in Japanese Patent No. 6513798, the radiation image captured by the radiation photoconductor is an image at a position outside of the body of the subject, and the biomagnetism detected by the biomagnetism detector is information at a position inside of the body of the subject. Therefore, it is not possible to superimpose biomagnetism data on the radiation image without change. To correctly superimpose the biomagnetism data on the radiation image, it is necessary to correct the radiation image according to the position of a magnetism generating part in the body of the subject. However, with the technology disclosed in Japanese Patent No. 6513798, such a correction cannot be performed easily.

SUMMARY OF THE INVENTION

According to an aspect of this disclosure, there is provided an image processing apparatus that includes a processor programmed to obtain a first radiation image of a subject captured from a first direction, obtain a second radiation image of the subject captured from a second direction that intersects the first direction, and either correct one of the first radiation image and the second radiation image based on positional information of a device for capturing the one of the first radiation image and the second radiation image, or correct another one of the first radiation image and the second radiation image based on information on a position of a specific region of the subject obtained from the one of the first radiation image and the second radiation image.

BRIEF DESCRIPTION OF THE DRAWINGS

FIG. 9 is a drawing illustrating examples of superimposed images generated by an image superimposing unit;

FIG. 10 is a drawing for explaining a variation of the method of correcting the first radiation image by the image corrector; and FIG. 11 is a drawing for explaining a variation of the method of correcting the first radiation image by the image corrector.

DESCRIPTION OF THE EMBODIMENTS

An embodiment of the present invention is described below with reference to the accompanying drawings.

(System Configuration of Imaging System)

Figure 1:
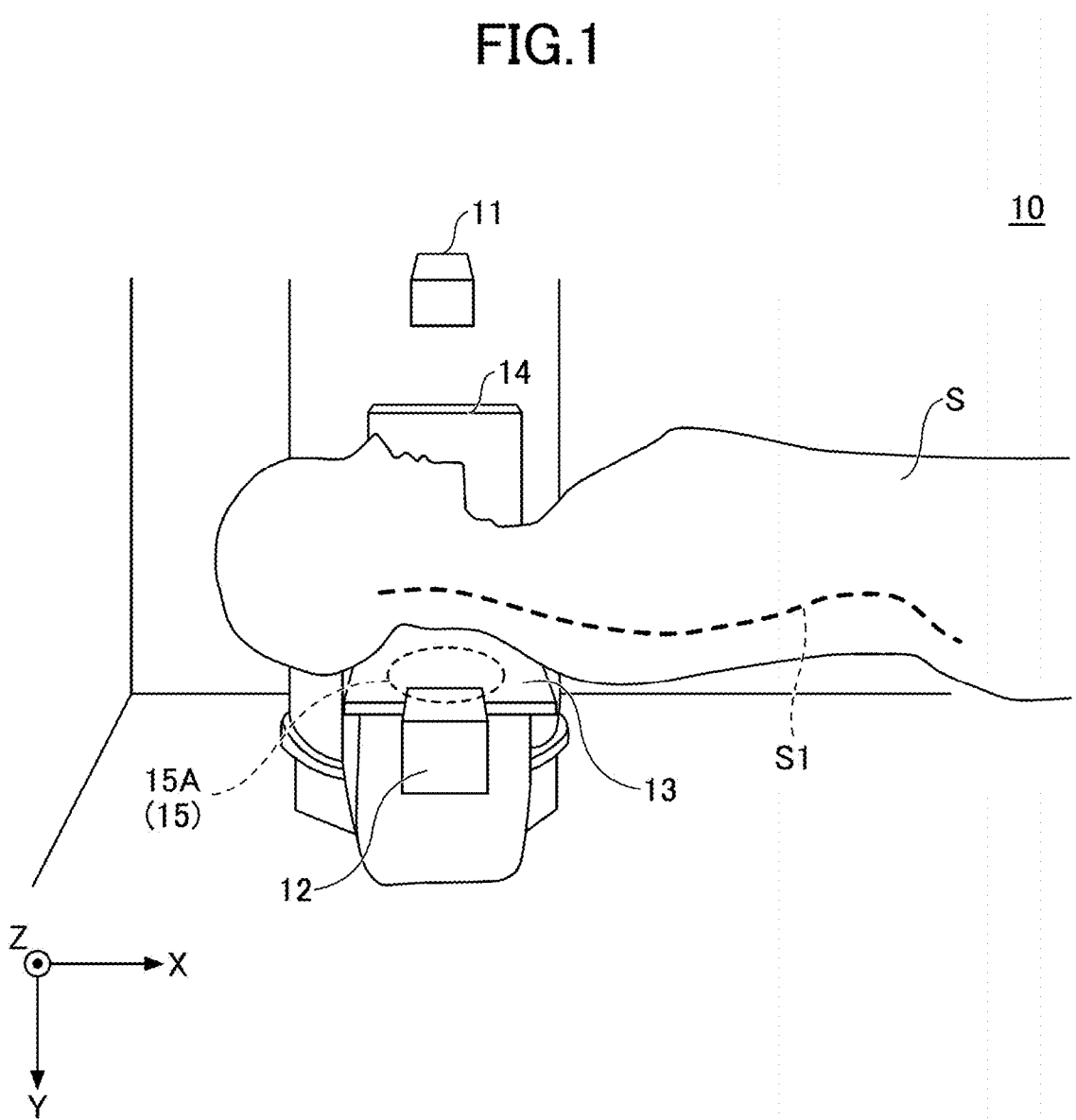
FIG. 1 is a drawing illustrating a system configuration of an imaging system according to an embodiment.

FIG. 1 is a drawing illustrating a system configuration of an imaging system 10 according to an embodiment. The imaging system 10 illustrated in FIG. 1 is capable of capturing a radiation image of a target region (a region to be imaged, a neck in the example illustrated of FIG. 1) of a subject S (for example, a human body). Also, the imaging system 10 can detect magnetism in the target region of the subject S, generate a current distribution image representing the current distribution in the target region of the subject S based on the detection result, superimpose the current distribution image on a radiation image, and output the superimposed image.

As illustrated in FIG. 1, the imaging system 10 includes a first radiation source 11, a second radiation source 12, a first imager 13, a second imager 14, and a magnetism detection device 15. In the present embodiment, for explanation purposes, a Y-axis direction is the height direction (the front and back directions of the subject S when the subject S is in the supine or prone position). Also, in the present embodiment, a Z-axis direction is the horizontal direction (the width direction of the subject S when the subject S is in the supine or prone position). Further, in the present embodiment, the direction orthogonal to each of the Y-axis and the Z-axis (the standing height direction of the subject S) is an X-axis direction.

The first radiation source 11 is positioned above the target region of the subject S. The first radiation source 11 emits radiation (for example, X-rays) from above the target region of the subject S toward the target region of the subject S. For example, the first radiation source 11 may be implemented by a known radiation emitting device.

The second radiation source 12 is positioned lateral to the target region of the subject S. The second radiation source 12 emits radiation (for example, X-rays) from a position lateral to the target region of the subject S toward the target region of the subject S. For example, the second radiation source 12 may be implemented by a known radiation emitting device.

The first imager 13 is positioned below the target region of the subject S to face the first radiation source 11 across the subject S. The first imager 13 captures a radiation image of the subject S from a position below the target region of the subject S (an example of a "first direction") by using the radiation emitted from the first radiation source 11 and transmitted through the subject S. That is, the first imager 13 captures a radiation image (which is hereafter referred to as a "first radiation image") of the subject S from a position below the subject S. The first imager 13 can output the captured first radiation image to an image processing apparatus 100 (see FIG. 2).

The second imager 14 is positioned lateral to the target region of the subject S to face the second radiation source 12 across the subject S from a position lateral to the target region of the subject S (an example of a "second direction"). The second imager 14 captures a radiation image of the subject S by using the radiation emitted from the second radiation source 12 and transmitted through the subject S. That is, the second imager 14 captures a radiation image (which is hereafter referred to as a "second radiation image") of the subject S from a position lateral to the subject S. The second imager 14 can output the captured second radiation image to the image processing apparatus 100 (see FIG. 2).

In the present embodiment, an imaging direction (the first direction) in which the first imager 13 captures an image and an imaging direction (the second direction) in which the second imager 14 captures an image are orthogonal to each other. However, the present invention is not limited to this example, and the imaging direction (the first direction) of the first imager 13 and the imaging direction (the second direction) of the second imager 14 may be substantially orthogonal to each other. That is, in the present embodiment, "intersection" between the imaging direction (the first direction) of the first imager 13 and the imaging direction (the second direction) of the second imager 14 may indicate that these directions are substantially orthogonal to each other. In the present application, "substantially orthogonal" indicates not only an angle of 90 degrees but also an angle of 90 degrees plus or minus 10 degrees. Also, in the present embodiment, the first radiation source 11, the first imager 13, the second radiation source 12, and the second imager 14 correspond to "devices configured to capture a radiation image".

The magnetism detection device 15 is provided at a position below the target region of the subject S and below the first imager 13, and detects magnetism in the target region of the subject S. The magnetism detection device 15 includes a magnetic sensor 15A. The magnetic sensor 15A includes multiple magnetism detection elements (not shown) arranged in the horizontal direction. The magnetic sensor 15A detects magnetism at each of multiple horizontal positions in the target region of the subject S with the corresponding magnetism detecting element. The magnetism detection device 15 can output magnetism detection data indicating magnetism detection values at the respective positions in the target region of the subject S detected by the magnetic sensor 15A, to the image processing apparatus 100 (see FIG. 2). For example, the magnetic sensor 15A may be implemented by a superconducting quantum interference device (SQUID) or an optically pumped atomic magnetometer (OPAM). In the present embodiment, the magnetism generating part in the target region of the subject S is a spinal cord S1. Accordingly, in the present embodiment, the magnetism detection device 15 detects magnetism emitted by the spinal cord or cauda equina nerve S1 in the target region (for example, the neck) of the subject S.

As illustrated in FIG. 1, the target region of the subject S is placed between the first radiation source 11 and the first imager 13 and between the second radiation source 12 and the second imager 14. Also, as illustrated in FIG. 1, the subject S is placed on, for example, a bed as necessary so that the subject S can easily maintain the lying posture.

(Functional Configuration of Image Processing Apparatus)

Figure 2:
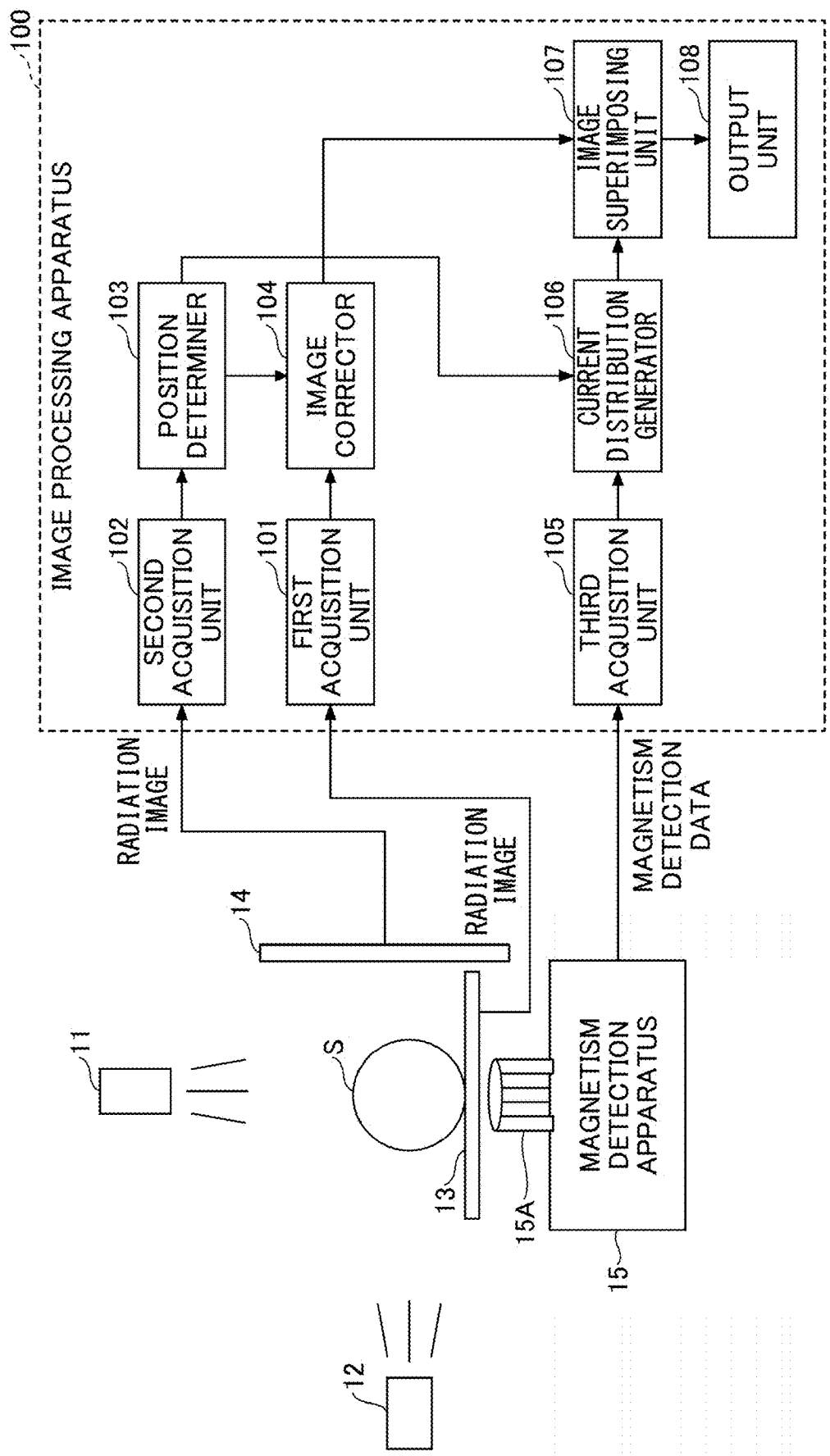
FIG. 2 is a drawing illustrating a functional configuration of an image processing apparatus according to an embodiment.

FIG. 2 is a drawing illustrating a functional configuration of the image processing apparatus 100 according to the embodiment. As illustrated in FIG. 2, the imaging system 10 further includes the image processing apparatus 100.

As illustrated in FIG. 2, the image processing apparatus 100 includes a first acquisition unit 101, a second acquisition unit 102, a position determiner 103, an image corrector 104, a third acquisition unit 105, a current distribution generator 106, an image superimposing unit 107, and an output unit 108.

The first acquisition unit 101 obtains a first radiation image (a radiation image of the subject S captured from a position below the subject S) captured by the first imager 13.

The second acquisition unit 102 obtains a second radiation image (a radiation image of the subject S captured from a position lateral to the subject S) captured by the second imager 14.

The position determiner 103 determines a position in the subject S at which magnetism is generated (an example of "information on a position of a specific region of a subject") relative to the imaging position of the first radiation image (i.e., an imaging position at which the first imager 13 captures an image) based on the second radiation image obtained by the second acquisition unit 102. In the present embodiment, the position determiner 103 determines a height r2 at a vertical position H2 of the spinal cord S1 of the subject S relative to the imaging position of the first radiation image (i.e., a vertical position H1 of the first imager 13) (see FIG. 4).

Figure 7:
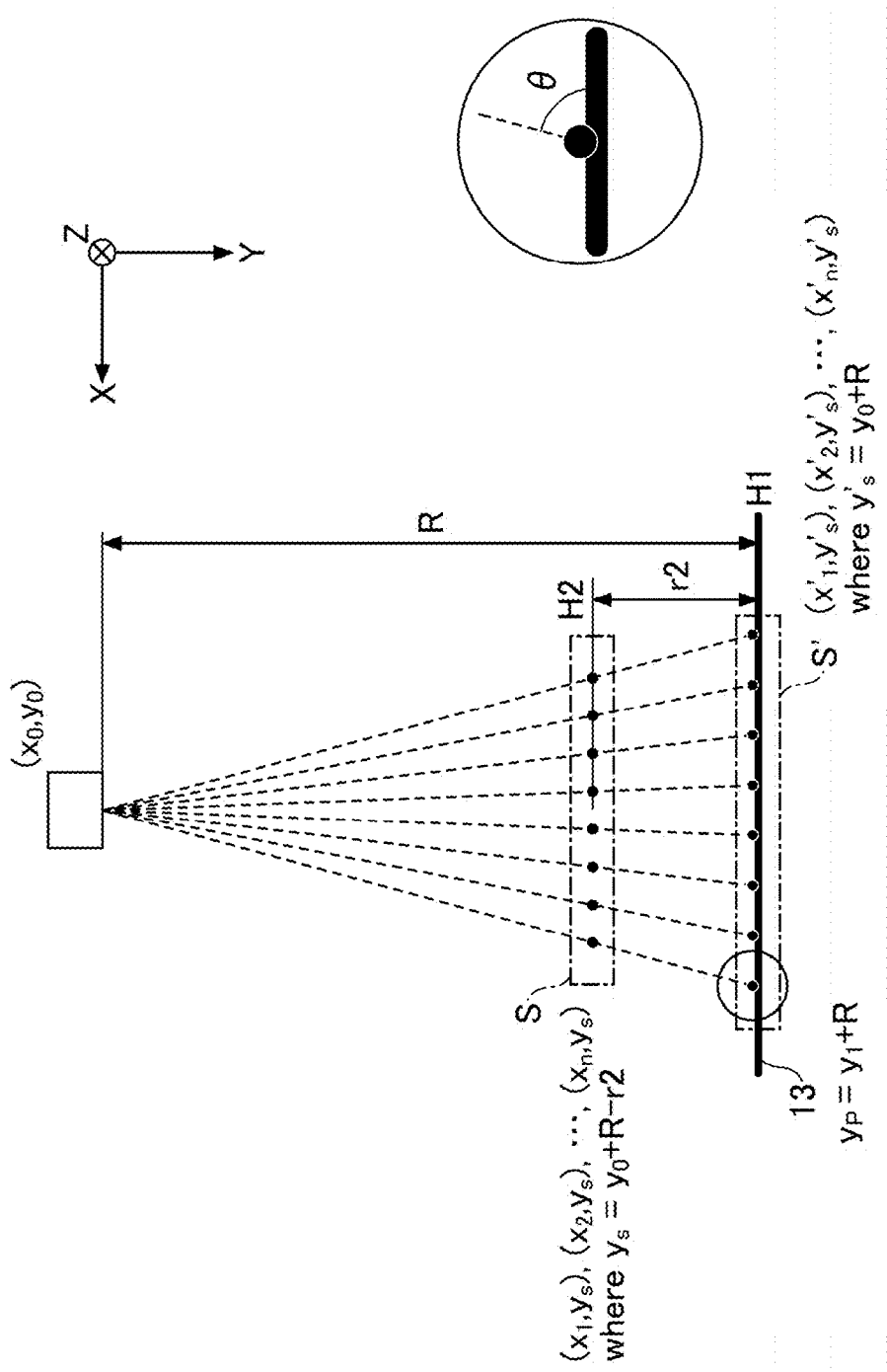
FIG. 7 is a drawing illustrating an example of a method of correcting a first radiation image by an image corrector.

The image corrector 104 corrects the first radiation image obtained by the first acquisition unit 101 based on the height r2 at the vertical position H2 of the spinal cord S1 of the subject S determined by the position determiner 103. Specifically, the image corrector 104 reduces the size of the first radiation image to a size corresponding to the vertical position H2 of the spinal cord S1 of the subject S determined by the position determiner 103. The size corresponding to the vertical position H2 indicates a size that the first radiation image may have if the first radiation image is captured by the first imager 13 at the vertical position H2. Thus, "correction of the image by the image corrector" indicates reducing a radiation image. Any method may be used to reduce the size of the first radiation image. For example, as illustrated in FIG. 7, the position of each pixel in the first radiation image after reduction may be calculated using a reduction coefficient. In this case, reduction coefficients applied to the respective pixels may be the same or may be different from each other.

The third acquisition unit 105 obtains magnetism detection data (that is, the magnetism detection value at each of multiple positions in the subject S) output from the magnetism detection device 15.

The current distribution generator 106 generates a current distribution image representing the current distribution in the target region of the subject S based on the magnetism detection data obtained by the third acquisition unit 105.

The image superimposing unit 107 generates a superimposed image in which the current distribution image generated by the current distribution generator 106 and the first radiation image corrected by the image corrector 104 are superimposed on each other.

The output unit 108 outputs the superimposed image generated by the image superimposing unit 107. For example, the output unit 108 displays the superimposed image on a display. However, the present invention is not limited to this example, and the output unit 108 may output the superimposed image with other output methods (for example, example, output to a memory or transmission to an external device).

The functional components of the image processing apparatus 100 described above may be implemented by one or more processing circuits. In the present application, examples of "processing circuits" include a processor programmed to execute functions according to software such as a processor implemented by an electronic circuit; and devices such as an application specific integrated circuit (ASIC), a digital signal processor (DSP), a field programmable gate array (FPGA), and other circuit modules designed to execute the functions of the image processing apparatus 100 described above.

(Process Performed by Image Processing Apparatus)

Figure 3:
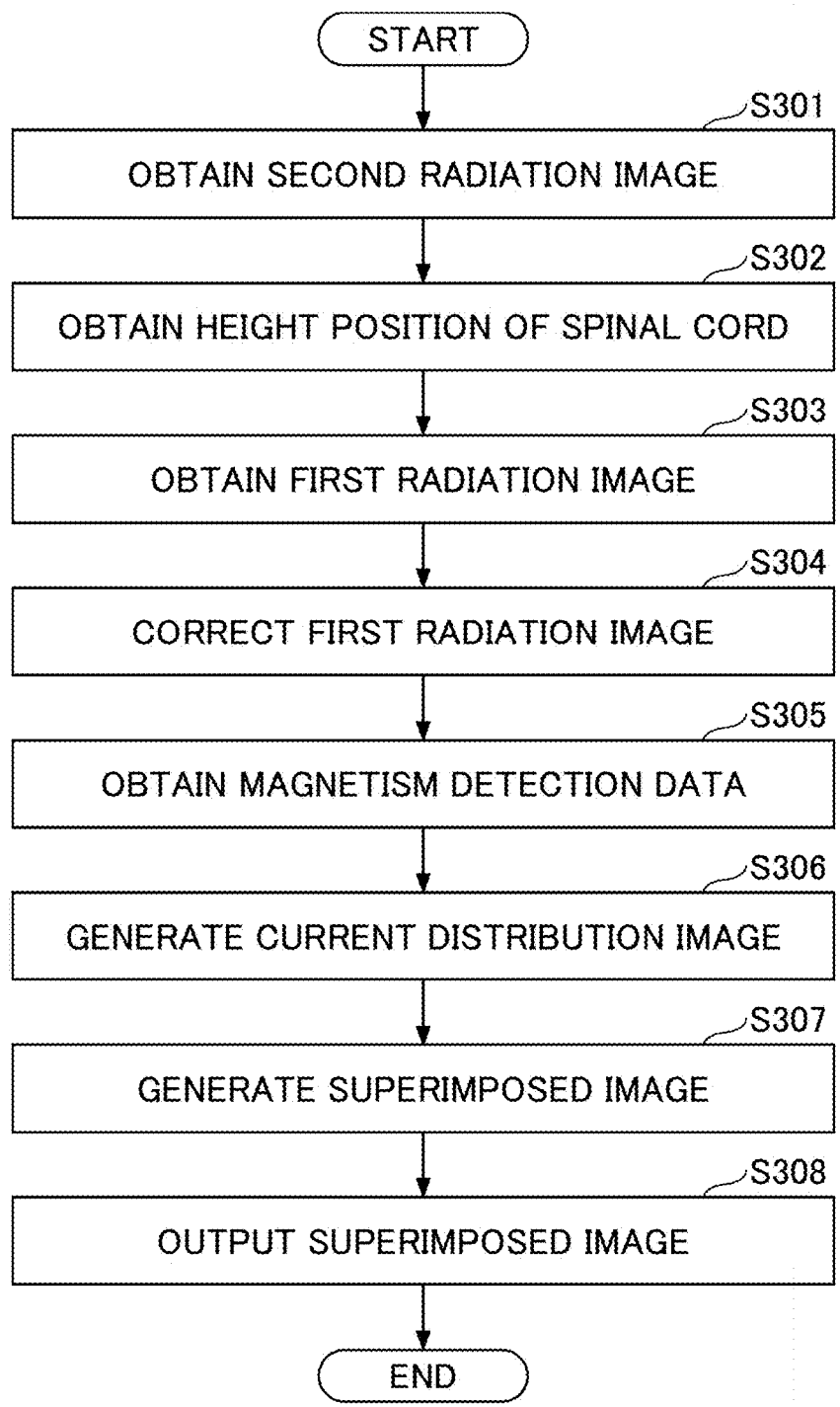
FIG. 3 is a flowchart illustrating a process performed by an image processing apparatus according to an embodiment.

FIG. 3 is a flowchart illustrating a process performed by the image processing apparatus 100 according to the embodiment.

First, the second acquisition unit 102 obtains the second radiation image (i.e., a radiation image of the subject S captured from a position lateral to the subject S) captured by the second imager 14 (step S301).

Next, the position determiner 103 determines the height r2 at the vertical position H2 of the spinal cord S1 of the subject S relative to the vertical position H1 of the first imager 13 based on the second radiation image obtained at step S301 (step S302). Specifically, for example, the height r2 may be determined by causing the output unit 108 to output the second radiation image on a display unit (not shown) and requesting an operator to specify (or locate) the position of the spinal cord S1 on a screen. Alternatively, the position determiner 103 may be configured to recognize the spinal cord S1 by machine learning at the position determiner 103 or using external machine learning and determine the height r2 based on the recognition result.

Next, the first acquisition unit 101 obtains the first radiation image (i.e., a radiation image of the subject S captured from a position below the subject S) captured by the first imager 13 (step S303).

Next, the image corrector 104 corrects the size of the first radiation image obtained at step S303 based on the height r2 at the vertical position H2 of the spinal cord S1 of the subject S determined at step S302 (step S304). Specifically, the image corrector 104 reduces the size of the first radiation image to a size corresponding to the vertical position H2 based on the ratio between a distance R between the first radiation source 11 and the first imager 13 and a distance (R−r2).

Next, the third acquisition unit 105 obtains the magnetism detection data (that is, the magnetism detection value of each of the multiple positions in the subject S) output from the magnetism detection device 15 (step S305).

Next, the current distribution generator 106 generates a current distribution image representing the current distribution in the target region of the subject S based on the magnetism detection data obtained at step S305 (step S306).

Next, the image superimposing unit 107 generates a superimposed image by superimposing the current distribution image generated at step S306 and the first radiation image corrected at step S304 on each other (step S307). Next, the output unit 108 outputs the superimposed image generated at step S307 (step S308). Then, the image processing apparatus 100 ends the process illustrated in FIG. 3.

In the above process, the second radiation image is obtained first. However, the present invention is not limited to this example, and the first radiation image may be obtained first. Still, however, in the present embodiment, the second radiation image is preferably obtained obtained first because the vertical position H2 of the spinal cord S1 of the subject S is determined based on the second radiation image. Also, in terms of preventing the misalignment due to the movement of the subject S, the first radiation image and the second radiation image are more preferably obtained substantially at the same time.

Also, in terms of preventing the misalignment due to the movement of the subject S, the imaging system 10 preferably includes two pairs of a radiation source and an imager. However, the present invention is not limited to this example, and the imaging system 10 may include, for example, one pair of a radiation source and an imager. In this case, the imaging system 10 may capture and obtain the first radiation image using the one pair of the radiation source and the imager as the first radiation source 11 and the first imager 13 (step S303), and capture and obtain the second radiation image by moving the one pair of the radiation source and the imager and using them as the second radiation source 12 and the second imager 14 (step S301).

Also, in terms of preventing the misalignment of radiation sources, the imaging system 10 preferably includes two radiation sources that are fixed or have positional reproducibility. However, the present invention is not limited to this example, and the imaging system 10 may include, for example, one radiation source. In this case, the imaging system 10 may capture and obtain the first radiation image by irradiating the subject S using the one radiation source as the first radiation source 11 (step S303), and capture and obtain the second radiation image by moving the one radiation source and irradiating the subject S using the one radiation source as the second radiation source 12 (step S301).

In addition, in terms of preventing the misalignment of imagers, the imaging system 10 preferably includes two imagers that are fixed or have positional reproducibility. However, the present invention is not limited to this example, and the imaging system 10 may include, for example, one imager. In this case, the imaging system 10 may capture and obtain the first radiation image using the one imager as the first imager 13 (step S303), and capture and obtain the second radiation image by moving the one imager and using the one imager as the second imager 14 (step S301).

The above-described process is based on the assumption that either the radiation source or the imager is implemented by two devices. However, the first radiation image and the second radiation image may be captured and obtained by combining the above-described steps and moving one radiation source and one imager.

(Method of Determining Height R2 at Vertical Position H2 of Spinal Cord S1 by Position Determiner)

Figure 4:
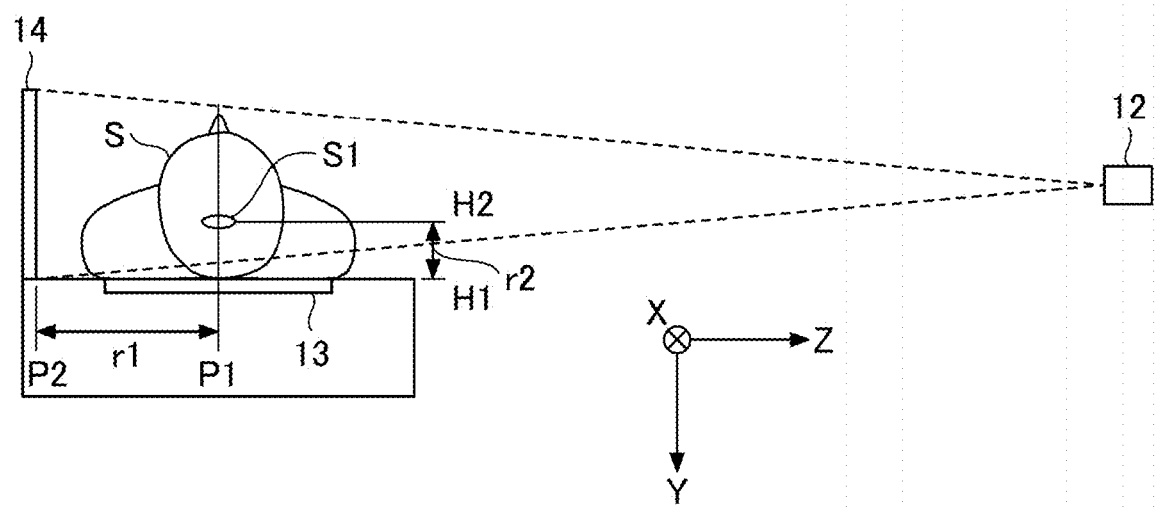
FIG. 4 is schematic diagram illustrating a positional relationship between the horizontal position of a spinal cord of a subject and the imaging position of a second radiation image.
Figure 5:
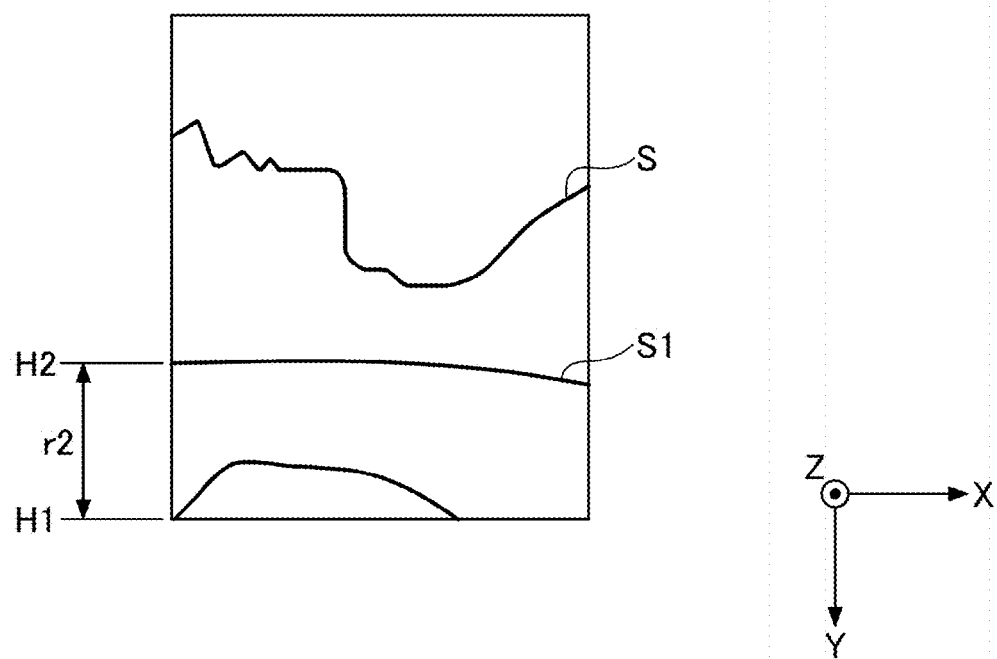
FIG. 5 is a drawing illustrating an example of a second radiation image corrected by a position determiner.

FIG. 4 is a schematic diagram illustrating the positional relationship between a horizontal position P1 of the spinal cord S1 of the subject S and an imaging position P2 of the second radiation image. FIG. 5 is a drawing illustrating an example of a second radiation image corrected by the position determiner 103.

As illustrated in FIG. 4, the horizontal position P1 of the spinal cord S1 in the subject S is the central position in the horizontal direction of the subject S. On the other hand, the imaging position P2 at which the second radiation image is captured by the second imager 14, is located farther from the second radiation source 12 than the horizontal position P1 of the spinal cord S1.

As illustrated in FIG. 4, because the second radiation source 12 is a point radiation source, the irradiation range of the second radiation source 12 gradually increases as the distance from the second radiation source 12 increases. Therefore, the size of the second radiation image captured by the second imager 14 at the imaging position P2 is larger than the size of an image captured at the horizontal position P1 of the spinal cord S1.

For the above reason, the position determiner 103 first identifies the horizontal position P1 of the spinal cord S1. For example, the subject S is placed on the bed such that the spinous process at the center of the spinal cord S1 in the horizontal direction is aligned with a linear marker provided in a predetermined position in the horizontal direction of the bed. Because the horizontal position P1 of the spinal cord S1 is aligned with the predetermined position in the horizontal direction of the bed, the position determiner 103 can easily determine the horizontal position P1 of the spinal cord S1. As another example, the subject S may be placed on the bed after attaching a marker coil to the spinous process of the spinal cord S1. In this case, the position determiner 103 can easily determine the horizontal position P1 of the spinal cord S1 based on the positional information of the marker coil.

Next, the position determiner 103 reduces the size of the second radiation image captured by the second imager 14 at a reduction percentage corresponding to a distance r1 between the determined horizontal position P1 of the spinal cord S1 and the imaging position P2 so that the size of the second radiation image is reduced to a size corresponding to the horizontal position P1 of the spinal cord S1. The size corresponding to the horizontal position P1 indicates a size that the second radiation image may have if the second radiation image is captured by the second imager 14 at the horizontal position P1. Specifically, the position determiner 103 stores (or inputs), in advance, information (corresponding to "positional information of a device that captures a radiation image") indicating the positional relationship between the position of the second radiation source 12 and the imaging position P2, and calculates the reduction percentage to be applied to the second radiation image based on the stored information and the information on the horizontal position P1 of the spinal cord S1.

Next, the position determiner 103 determines the vertical position H2 of the spinal cord S1 in the corrected second radiation image. For example, the position determiner 103 displays the corrected second radiation image on a display and requests an operator to specify the vertical position H2 of the spinal cord S1 in the corrected second radiation image.

Then, based on the specified vertical position H2 of the spinal cord S1 in the corrected second radiation image, the position determiner 103 calculates the height r2 from the vertical position H1 to the vertical position H2.

Here, the size of each pixel in the corrected second radiation image becomes smaller than the size of each pixel in the second radiation image before correction according to the reduction percentage used for the correction of the second radiation image.

For example, when the size of each pixel in the second radiation image before correction is "0.15 mm" and the reduction percentage used for the correction of the second radiation image is "80%", the size of each pixel in the corrected second radiation image becomes "0.12 mm".

Then, the position determiner 103 calculates the height r2 from the vertical position H1 to the vertical position H2 by multiplying the size of each pixel in the second radiation image before correction by the number of pixels from the vertical position H1 to the vertical position H2 in the corrected second radiation image.

For example, when the size of each pixel in the corrected second radiation image is "0.12 mm" and the number of pixels from the vertical position H1 to the vertical position H2 in the corrected second radiation image is "650", the position determiner 103 calculates the height r2 from the vertical position H1 to the vertical position H2 as "78 mm".

Here, depending on the positional relationship between the second radiation source 12 and the second imager 14, the vertical position H1 may not be included in the second radiation image. In this case, it is preferable to provide a radiation marker whose positional relationship with the vertical position H1 is known at a position where the radiation marker is certainly captured in the second radiation image, and to determine the vertical position H1 based on the radiation marker.

(Method of Correcting First Radiation Image by Image Corrector)

Figure 6:
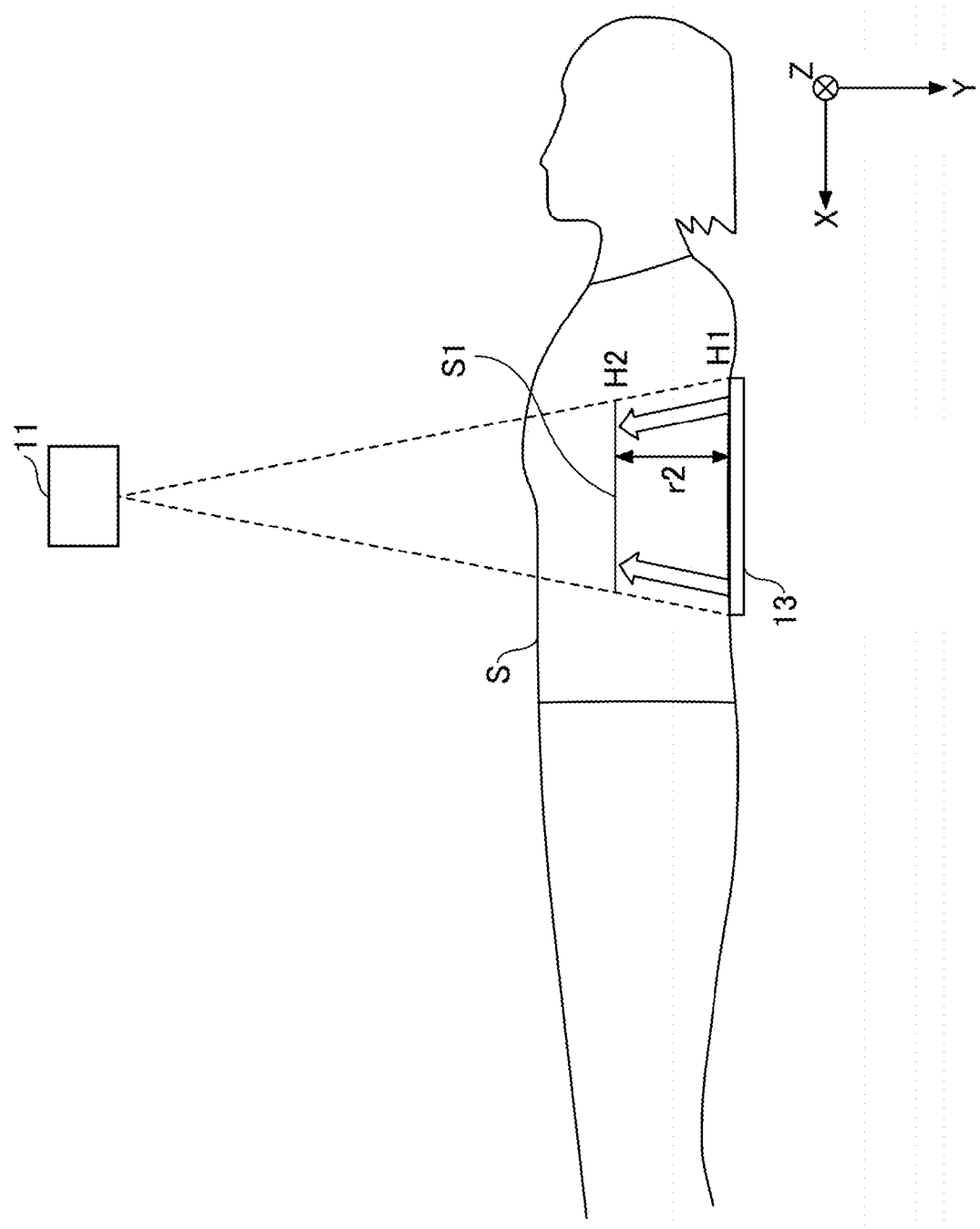
FIG. 6 is a schematic diagram illustrating a positional relationship between the vertical position of a spinal cord of a subject and the vertical position of a first imager.

FIG. 6 is a schematic diagram illustrating the positional relationship between the vertical position H2 of the spinal cord S1 of the subject S and the vertical position H1 of the first imager 13.

As illustrated in FIG. 6, the vertical position H2 of the spinal cord S1 in the subject S is in the body of the subject S. On the other hand, the vertical position H1 of the first radiation image captured by the first imager 13 is outside of the body of the subject S and is located farther from the first radiation source 11 than the vertical position H2 of the spinal cord S1.

As illustrated in FIG. 6, because the first radiation source 11 is a point radiation source, the irradiation range of the first radiation source 11 gradually increases as the distance from the first radiation source 11 increases. For this reason, the size of the first radiation image captured by the first imager 13 at the vertical position H1 is greater than a size corresponding to the vertical position H2 of the spinal cord S1. Therefore, the image corrector 104 corrects the first radiation image so that the size of the first radiation image is reduced to the size corresponding to the vertical position H2 of the spinal cord S1.

FIG. 7 is a drawing illustrating an example of a method of correcting the first radiation image by the image corrector 104. In FIG. 7, for description purposes, the spinal cord S1 of the subject S at the vertical position H2 is represented by a set of n black dots. Also, in FIG. 7, a first radiation image S' captured by the first imager 13 at the vertical position H1 using the radiation emitted from the first radiation source 11 toward the subject S is similarly represented by a set of n black dots. Further, in FIG. 7, the direction in which the radiation is emitted from the first radiation source 11 is defined as the Y axis, and the direction orthogonal to the Y axis is defined as the X axis.

Here, referring to a black dot $x'_1$ in the first radiation image S', an angle θ formed between the radiation emitted from the first radiation source 11 and the first imager 13 at the black dot $x'_1$ is expressed by θ=arc tan $(R/(x'_1-x_0))$. Here, R is a known distance from the first radiation source 11 to the first imager 13, and $x_0$ is the position of the first radiation source 11 on the X axis. Accordingly, the relationship between a black dot $x_1$ in the subject S and the black dot $x'_1$ in the first radiation image S' is represented by $(x_1-x_1) \tan \theta = r2$, which can be deformed into $x_1 = r2/\tan \theta + x'_1$. Here, r2 is the height from the vertical position H1 to the vertical position H2, which has already been determined by the position determiner 103.

The image corrector 104 obtains the position at the vertical position H2 of the subject S for each of pixels constituting the first radiation image S' in a similar manner and thereby corrects the first radiation image S' to a size corresponding to the vertical position H2 of the subject S.

(Examples of Current Distribution Images)

Figure 8:
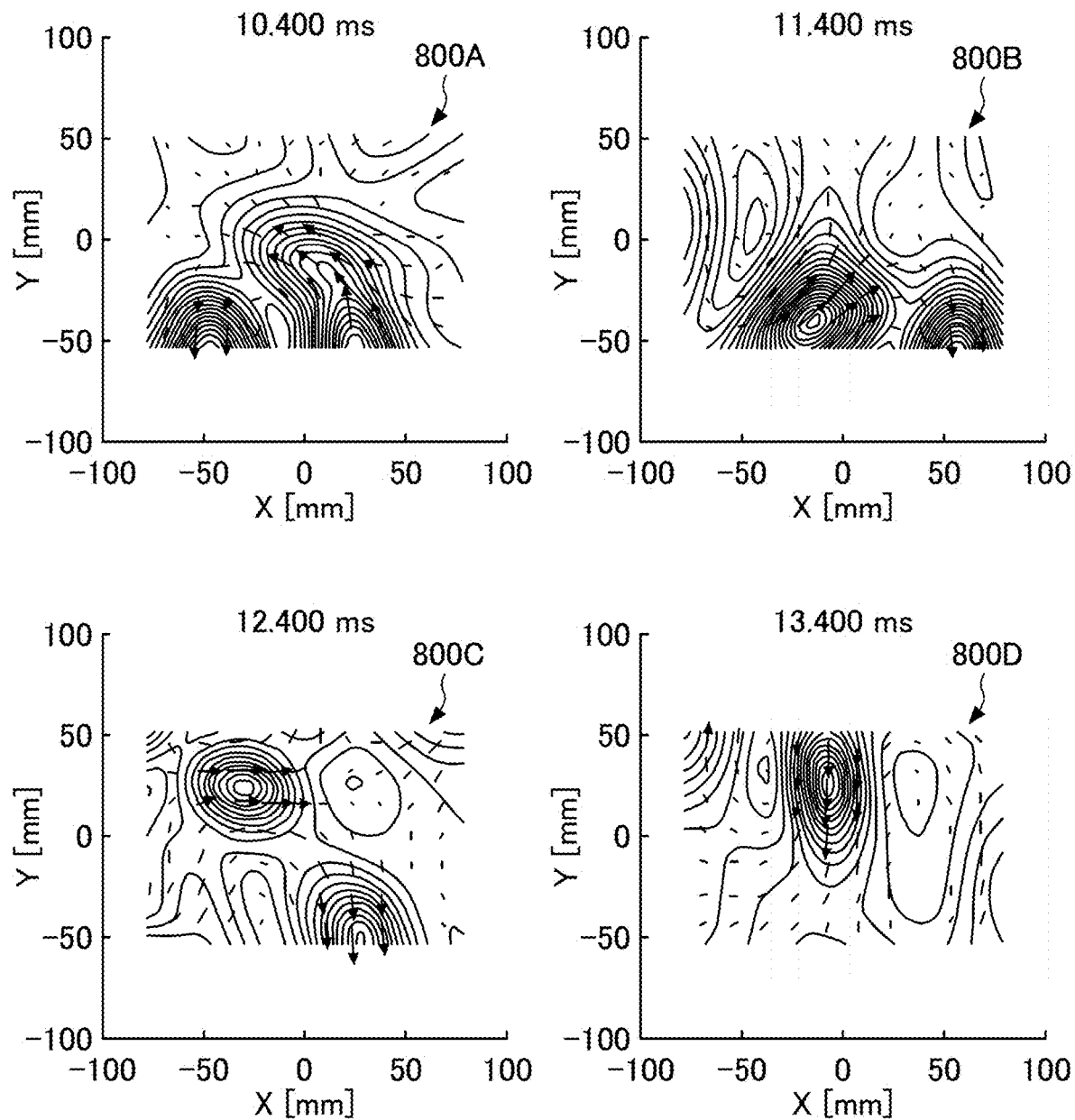
FIG. 8 is a drawing illustrating examples of current distribution images generated by a current distribution generator.

FIG. 8 is a drawing illustrating examples of current distribution images generated by the current distribution generator 106.

Current distribution distribution images 800A, 800B, 800C, and 800D illustrated in FIG. 8 represent time transition of the current distribution of neural activity currents in a target region (in this example, the lumbar region) of the subject S and are generated by the current distribution generator 106 based on magnetism detection data output from the magnetism detection device 15. In FIG. 8, the time (10.400 ms, 11.400 ms, 12.400 ms, or 13.400 ms) elapsed from the timing when electrical stimulation was given to the subject S (particularly, a fibular nerve in a fibular head in this example) is indicated in each of the current distribution images 800A, 800B, 800C, and 800D. In each of the current distribution images 800A, 800B, 800C, and 800D, the current distribution is represented by current contour lines. The current is strong where the lines are dense, and the current is weak where the lines are sparse. Also, arrows indicate the directions of currents at respective positions.

(Examples of Superimposed Images)

FIG. 9 is a drawing illustrating examples of superimposed images generated by the image superimposing unit 107. Each of superimposed images 900A, 900B, 900C, and 900D illustrated in FIG. 9 is generated by the image superimposing unit 107 by superimposing the corresponding one of of the current distribution images 800A, 800B, 800C, and 800D illustrated in FIG. 8 on the first radiation image (a radiation image of a target region (in this example, the lumbar region) of the subject S) corrected by the image corrector 104. Accordingly, each of the superimposed images 900A through 900D includes both of the image of a spine S1' of the subject S represented by the first radiation image and the current distribution around the spine S1' represented by the corresponding one of the current distribution images 800A through 800D. In the example illustrated in FIG. 9, to facilitate the understanding, the outline of the spine S1' in the first radiation image in the superimposed image 900A is emphasized.

Here, the first radiation image used for each of the superimposed images 900A through 900D is corrected by the image corrector 104 to have a size corresponding to the vertical position H2 of the spine S1' of the subject S. Also, the current distribution images 800A through 800D used for the superimposed images 900A through 900D are generated by the current distribution generator 106 to have a size corresponding to the vertical position H2 of the spine S1'.

That is, both of the first radiation image and the current distribution images 800A through 800D used to generate the superimposed images 900A through 900D have a size corresponding to the same vertical position (vertical position H2). Therefore, in the superimposed images 900A through 900D, both the image of the spine S1' of the subject S represented by the first radiation image and the current distributions around the spine S1' represented by the current distribution images 800A through 800D are presented with high positional accuracy.

(Variation of Image Correction Method)

FIGS. 10 and 11 are drawings for explaining a variation of the method of correcting the first radiation image by the image corrector 104. FIG. 10 illustrates physical features depicted in the second radiation image. FIG. 11 illustrates physical features depicted in the first radiation image. In the example illustrated in FIGS. 10 and 11, the outline of the spine S1' in each of the first radiation image and the second radiation image is emphasized to facilitate the understanding. Also, in the example illustrated in FIGS. 10 and 11, the imaging range of the first radiation image illustrated in FIG. 11 is greater than the imaging range of the second radiation image illustrated in FIG. 10.

In the example illustrated in FIGS. 10 and 11, the lower ends of pedicles of vertebral arch S2 in the spine S1', an upper end S3U of the spinous process, and a lower end S3L of the spinous process are used as the feature points extracted by the image corrector 104. In the example illustrated in FIGS. 10 and 11, each of the lower ends of the pedicles of vertebral arch S2 is marked with an "x".

When the positional relationship between the first radiation source 11 and the first imager 13 is unknown, as illustrated in FIGS. 10 and 11, the image corrector 104 may extract common physical features from the first radiation image and the second radiation image as another example of "information on a position of a specific region of a subject", and may correct the size of the first radiation image based on the positional relationship (e.g., the ratio of distances between multiple physical features) between the position of a physical feature in the first radiation image and the position of a physical feature in the second radiation image.

The image corrector 104 can extract the positions of multiple physical features in the standing height direction (the X-axis direction) of the subject S from each of the first radiation image and the second radiation image, and therefore can correct the first radiation image in the standing height direction (the X-axis direction) of the subject S using a correction coefficient obtained from the multiple physical features. On the other hand, the image corrector 104 cannot extract the positions of multiple physical features in the width direction (the Z-axis direction) of the subject S from the second radiation image. Therefore, the image corrector 104 may be configured to correct the first radiation image in the width direction (the Z-axis direction) of the subject S using the same correction coefficient as that used for the correction of the first radiation image in the vertical direction.

An aspect of this disclosure makes it possible to easily correct a radiation image according to the position of a specific region in the body of a subject.

An image processing apparatus, an imaging system, an image processing method, and a storage medium according to an embodiment of the present invention are described above. However, the present invention is not limited to the specifically disclosed embodiment, and variations and modifications may be made without departing from the scope of the present invention.

What is claimed is:

1. An image processing apparatus, comprising:
a processor programmed to
obtain a first radiation image of a subject captured from a first direction, obtain a second radiation image of the subject captured from a second direction that intersects the first direction, correct one of the first radiation image and the second radiation image based on information on a position of a specific region of the subject obtained from one of the first radiation image and the second radiation image, wherein the correction of one of the first radiation image and the second radiation image based on information on the position of the specific region of the subject includes to:

determine a position of a magnetism generating part of the subject in one of the first radiation image and the second radiation image, and correct one of the first radiation image and the second radiation image to a size corresponding to the determined position of the magnetism generating part based on the position of the magnetism generating part, the position of the magnetism generating part being the information on the position of the specific region of the subject.

2. The image processing apparatus as claimed in claim 1, wherein
the processor is programmed to correct one of the first radiation image and the second radiation image to the size corresponding to the position of the magnetism generating part based on a distance between the position of the magnetism generating part and an imaging position of one of the first radiation image and the second radiation image.

3. The image processing apparatus as claimed in claim 1, wherein the processor is further programmed to
obtain magnetism detection data from a magnetism detection device that detects magnetism emitted by the magnetism generating part, generate a current distribution image representing current distribution in the subject based on the magnetism detection data, and generate a superimposed image by superimposing the generated current distribution image on one of the first radiation image and the second radiation image that is corrected.

4. The image processing apparatus as claimed in claim 1, wherein the magnetism generating part is a spinal cord or a cauda *equina* nerve of the subject.

5. The image processing apparatus as claimed in claim 1, wherein
the first direction is a front direction or a back direction of the subject; and
the second direction is a right-side direction or a left-side side direction of the subject.

6. An imaging system, comprising:
the image processing apparatus as claimed in claim 1;
at least one imaging device configured to capture the first radiation image and the second radiation image; and
at least one radiation source configured to irradiate the subject with radiation when the first radiation image and the second radiation image are captured.

7. An image processing apparatus, comprising:
a processor programmed to
obtain a first radiation image of a subject captured from a first direction,
obtain a second radiation image of the subject captured from a second direction that intersects the first direction,
correct one of the first radiation image and the second radiation image based on information on a position of a specific region of the subject obtained from one of the first radiation image and the second radiation image, wherein the correction of one of the first radiation image and the second radiation image based on information on the position of the specific region of the subject includes to:

determine a position of a magnetism generating part of the subject in one of the first radiation image and the second radiation image, extract a physical feature, which is included in both of the first radiation image and the second radiation image, from the first radiation image and the second radiation image, determine a position of the physical feature, and correct one of the first radiation image and the second radiation image to a size corresponding to a position of a magnetism generating part of the subject based on a positional relationship between a position of the physical feature in one of the first radiation image and the second radiation image and a position of the physical feature in one of the first radiation image and the second radiation image.

8. The image processing apparatus as claimed in claim 7, wherein
the physical feature uses information about at least one of:
a lower end of pedicle of vertebral arch in a spine, an upper end of a spinous process, and a lower end of the spinous process.

9. An image processing method, comprising:
obtaining a first radiation image of a subject captured from a first direction;
obtaining a second radiation image of the subject captured from a second direction that intersects the first direction;
correcting one of the first radiation image and the second radiation image based on information on a position of a specific region of the subject obtained from one of the first radiation image and the second radiation image; wherein the correction of the first radiation image or the second radiation image includes:
determining a position of a magnetism generating part of the subject in one of the first radiation image and the second radiation image; and
correcting one of the first radiation image and the second radiation image to a size corresponding to the determined position of the magnetism generating part based on the position of the magnetism generating part, the position of the magnetism generating part being the information on the position of the specific region of the subject.

10. A non-transitory computer-readable storage medium storing a program for causing a computer to execute the method according to claim 9.

11. An image processing method, comprising:
obtaining a first radiation image of a subject captured from a first direction;
obtaining a second radiation image of the subject captured from a second direction that intersects the first direction;
correcting one of the first radiation image and the second radiation image based on information on a position of a specific region of the subject obtained from one of the first radiation image and the second radiation image; wherein the correction of one of the first radiation image and the second radiation image based on information on the position of the specific region of the subject includes:

determining a position of a magnetism generating part of the subject in one of the first radiation image and the second radiation image;

extracting a physical feature, which is included in both of the first radiation image and the second radiation image, from the first radiation image and the second radiation image;

determining a position of the physical feature; and correcting one of the first radiation image and the second radiation image to a size corresponding to a position of a magnetism generating part of the subject based on a positional relationship between a position of the physical feature in one of the first radiation image and the second radiation image and a position of the physical feature in one of the first radiation image and the second radiation image.

12. A non-transitory computer-readable storage medium storing a program for causing a computer to execute the method according to claim 11.

13. The image processing apparatus as claimed in claim 11, wherein the physical feature uses information about at least one of:

a lower end of pedicle of vertebral arch in a spine, an upper end of a spinous process, and a lower end of the spinous process.

\* \* \* \* \*